United States Patent [19]

Runge

[11] 4,058,855
[45] Nov. 22, 1977

[54] CARDIAC PUMPING DEVICE

[76] Inventor: Thomas M. Runge, 2501 Galewood Place, Austin, Tex. 78701

[21] Appl. No.: 760,322

[22] Filed: Jan. 18, 1977

Related U.S. Application Data

[63] Continuation-in-part of Ser. No. 657,703, Feb. 12, 1976, Pat. No. 4,004,299.

[51] Int. Cl.² .......................... A61F 1/24; A61M 1/03
[52] U.S. Cl. ........................................ 3/1.7; 128/1 D; 128/DIG. 3; 417/412; 417/521; 92/31; 74/57
[58] Field of Search ......... 3/1.7, 1; 128/1 D, DIG. 3; 74/57; 92/31; 417/412, 521

[56] References Cited

U.S. PATENT DOCUMENTS

| | | | |
|---|---|---|---|
| 2,245,457 | 6/1941 | Brassell | 74/57 |
| 2,361,821 | 10/1944 | Crowe et al. | 74/57 |
| 2,815,715 | 12/1957 | Tremblay | 128/DIG. 3 |
| 3,379,191 | 4/1968 | Harvey | 3/1.7 |
| 3,496,878 | 2/1970 | Hargest et al. | 3/1.7 X |
| 3,513,486 | 5/1970 | Cotton De Bennetot et al. | 3/1.7 |
| 3,771,173 | 11/1973 | Lamb | 3/1.7 |
| 3,860,968 | 1/1975 | Shapiro | 3/1.7 |

Primary Examiner—Ronald L. Frinks
Attorney, Agent, or Firm—B. P. Fishburne, Jr.

[57] ABSTRACT

A pulsatile flow pumping unit adapted to serve as a total cardiac replacement device, a cardiac assist pump for orthotopic placement, for extracorporeal application in conjunction with a membrane oxygenator for cardiopulmonary support during surgery or critical illnesses, for pulsatile flow coronary artery perfusion, and for filling and emptying of an aortic diastolic augmentation balloon for cardiac assist is provided. The pumping unit features simplicity of construction, comparative economy and reliability by utilizing a minimum number of working parts including a large diameter slitted rotary driver and cam operated follower means which avoids close machining tolerances and attendant high cost of manufacturing. The device automatically adjusts its rate of pumping in accordance with both preload (filling pressure) and afterload (pulmonic and systemic pressure) and in addition modifies its stroke volume in a downward direction when confronted with high afterload. The automatic adjustment of the device during operation depending on several variables is accomplished without electronic control or monitoring.

12 Claims, 9 Drawing Figures

CARDIAC PUMPING DEVICE

CROSS-REFERENCE TO RELATED APPLICATION

This application is a continuation-in-part of prior copending application Ser. No. 657,703, filed Feb. 12, 1976, for CARDIAC REPLACEMENT AND ASSIST DEVICES, now U.S. Pat. No. 4,004,299.

BACKGROUND OF THE INVENTION

The above-noted prior application discloses a pulsatile flow, synchronous ventricular ejection pump which closely simulates the operation of the natural heart. The prior device has the ability during operation to automatically regulate pumping rate as a function of filling pressure. The present invention adds to this the capability of automatically regulating stroke volume as a function of afterload, thus rendering the invention even closer in operation to the natural heart.

The device of the prior application, while notably satisfactory for its intended purposes involves a center rotary drive shaft for a pumping disc which cyclically compresses and forces blood out of a pair of blood compatible sacs which simulate the left and right ventricles of the heart. The shaft has a partially roofed groove and other features which render it somewhat difficult and costly to machine. The present invention offers a substantial improvement over the prior device by utilization of a simpler and much less expensive drive means for the disc which compresses the two sacs or blood chambers of the pump. All of this is accomplished under the invention without diminishing the operational capabilities of the prior device and in fact, as stated, automatic control of pumping rate and stroke volume responsive to variations in filling pressure and pulmonic and systemic pressure, respectively, are both achieved under the invention whereas, in the prior device, automatic control of pumping rate only as a function of filling pressure is achieved.

It should be understood that the invention may also have applications apart from the cardiovascular system; that is, would be suitable for pumping blood outside of the body in cardiopulmonary bypass hardware, and it may also have industrial applications where automatic response to preload and afterload are desired in conjunction with pulsatile flow.

Other features and advantages of the invention will be recognized by those skilled in the art during the course of the following detailed description.

DETAILED DESCRIPTION

Figure 1:
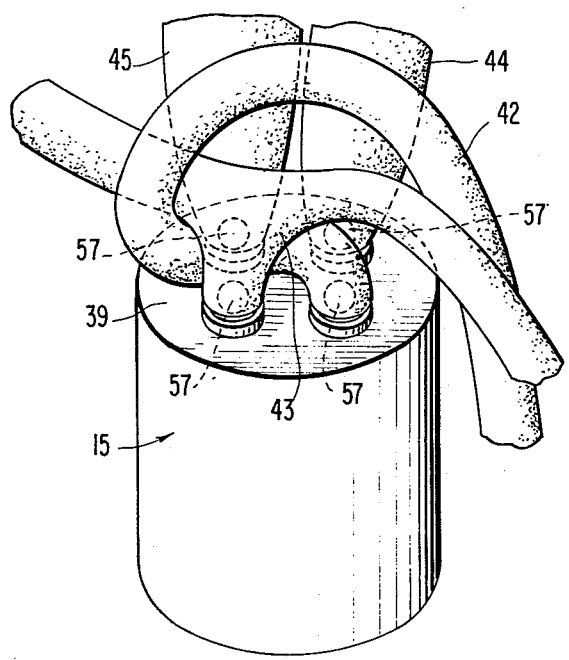
FIG. 1 is a partly schematic perspective view of the invention according to one embodiment thereof as a four chambered heart.
Figure 7:
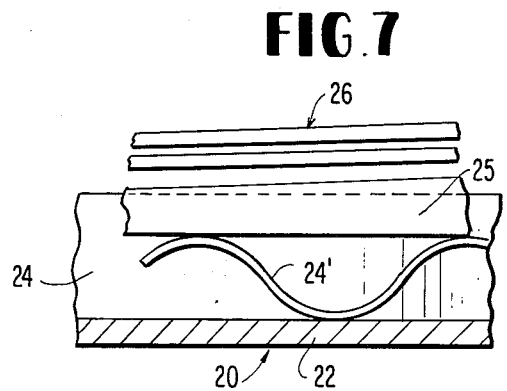
FIG. 7 is a fragmentary vertical section taken through a driving cup side wall and showing a spring and associated elements within an annular slot of the side wall.

Referring to the drawings in detail wherein like numerals designate like parts throughout, the numeral 15 designates a cylindrical outer housing or shell which will be covered with Dacron reinforced Silastic, or other tissue compatible material when the invention is utilized as a cardiac replacement unit. The lower end of the shell 15 is internally shouldered at 16 to accept and position a pancake electric motor 17 adapted to be powered by electromagnetic induction across the intact skin of the recipient from a primary external coil, not shown, to a secondary subcutaneous coil. Such powering means are well known in the art and need not be described further for a proper understanding of the invention. The induction motor 17 is of the type disclosed in the above-referenced prior application. The pancake motor 17 has an upstanding central output shaft 18 which is preferably square in cross section for socketing engagement within a central bottom square socket 19 of a rotary driving cup 20.

The cup 20 is cylindrical and is open at the top and includes a side wall 21 and a bottom wall 22. The driving cup has a center upstanding bullet-like cam post 23 rising from the bottom wall 22 and integral therewith, the socket 19 being formed in the cam post 23. The elements 18, 19 and 23 lie on the main longitudinal axis of the outer shell 15 and the parts are concentrically arranged.

The cylindrical side wall 21 of the driving cup 20 has a narrow annular slot 24 formed therein and opening through the top of the cup side wall 21. This slot receives the lower solid skirt 25 of a thin walled cylindrical rotary driving sleeve 26, the driving sleeve having a continuous narrow spiral slit 27 of uniform pitch over most of its length. Within the slot 24 below the skirt 25 and biasing the driving sleeve 26 upwardly relative to the cup 20 is a sinusoidal light spring 24', or plural springs, or an equivalent resilient means.

Figure 4A:
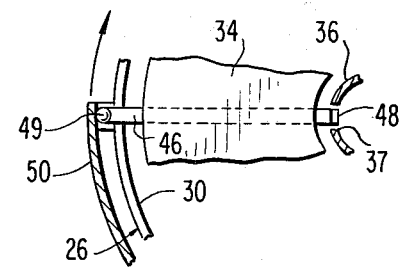
FIG. 4A is a fragmentary horizontal section, similar to FIG. 4, showing the beginning of a camming action on a radially shiftable disc driving element.
Figure 4:
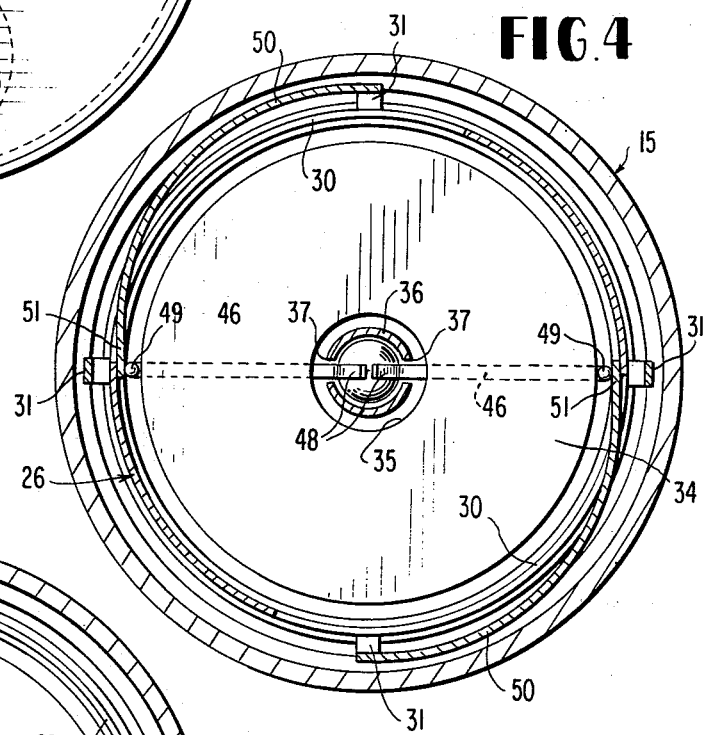
FIG. 4 is a horizontal section taken on line 4—4 of FIG. 2.
Figure 5:
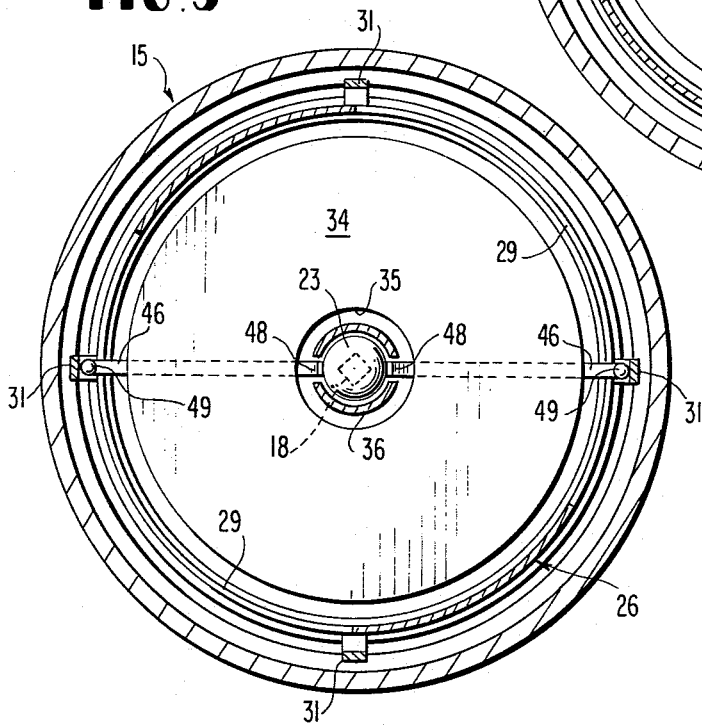
FIG. 5 is a horizontal section taken on line 5—5 of FIG. 2.

Immediately above the lower skirt 25 at diametrically opposite points on the sleeve, the slit 27 has widened exit sections 29 extending circumferentially of the sleeve 26 for approximately 120 degrees each, FIG. 5. Similarly, below an upper end portion 28 of the sleeve 26 at diametrically opposite points, the slit 27 has widened entrance sections 30 extending circumferentially of the sleeve for approximately 120 degrees each, FIG. 4.

Figure 2:
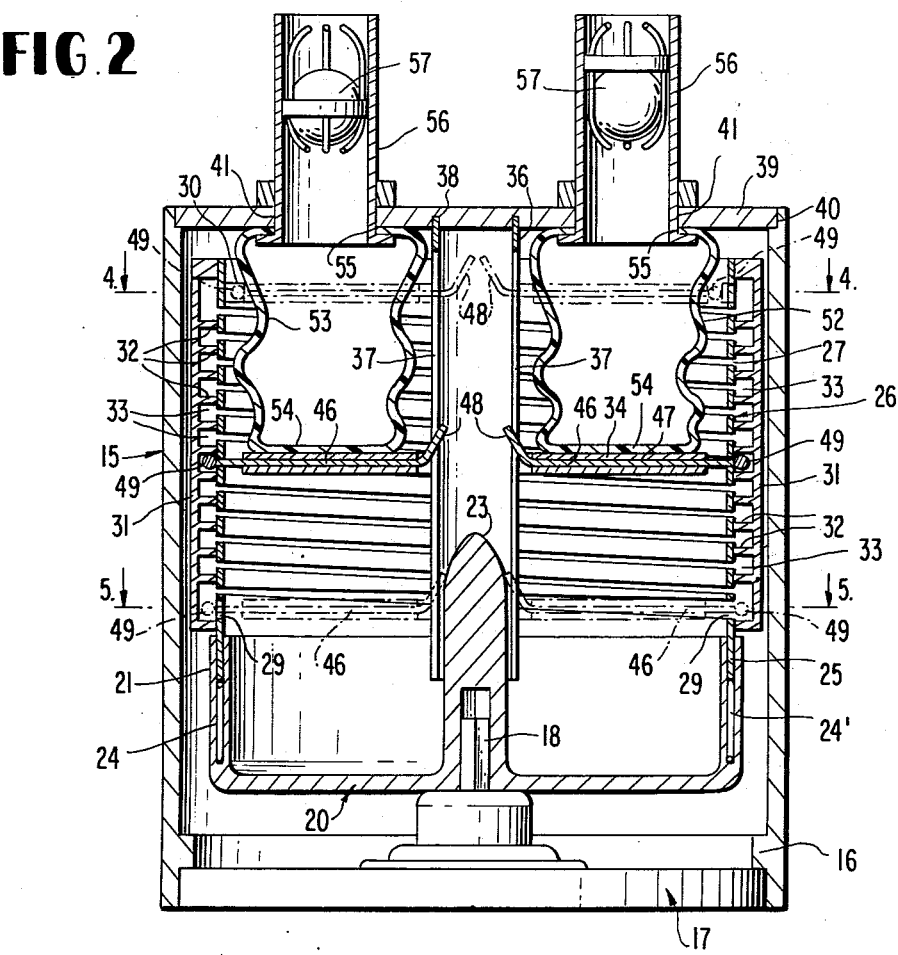
FIG. 2 is an enlarged central vertical section taken on line 2—2 of FIG. 3.
Figure 3:
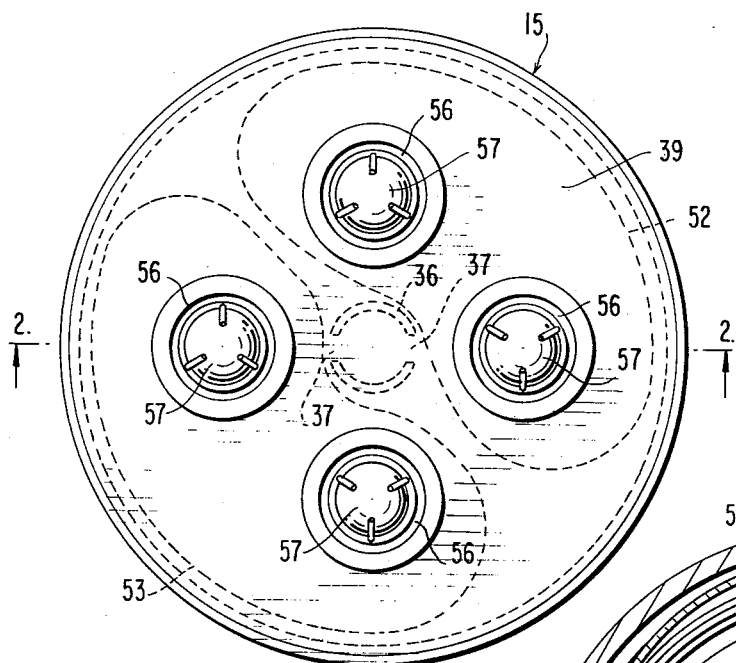
FIG. 3 is a plan view of the invention.

To render the thin walled rotary driving sleeve 26 stable and sufficiently rigid, preferably four equidistantly spaced parallel longitudinal bars 31 having internal equidistantly spaced lateral teeth 32 are attached fixedly to the periphery of the driving sleeve 26. Other forms of stabilizing means for the driving sleeve 26 may be employed. As shown in FIG. 2, the spaces 33 between teeth 32 of the stabilizing bars 31 communicate with the continuous spiral slit 27 for an important purpose, to be described. In some cases, in lieu of the lower skirt 25 entering the slot 24 of driving cup 20, lower extensions of the stabilizing bars 31 may be received drivingly in four side wall openings or sockets of the cup side wall 21. The preferred arrangement, however, is shown in the drawings.

The pumping device of the invention further comprises a flat annular disc 34 or plate having a central clearance aperture 35 which receives a center stationary axial guidance tube 36 having opposite side longitudinal slots 37. The stationary guidance tube 36 has its upper end anchored firmly in a groove 38, FIG. 2, of a preferably flat cover plate 39 or lid for the outer shell 15, the lid being seated in an upper end recess 40 of the outer shell, FIG. 2. Like the outer shell, the lid 39 may be covered with Dacron reinforced Silastic. As in the prior referenced patent application, the lid 39 has four orifices 41 through which connections to the aorta 42 and pulmonary artery 43 are made, as well as connections to left and right atrium elements 44 and 45, FIG. 1.

The disc 34 is spanned diametrically by a pair of drive arms 46 which are held slidably in radial passages 47 of the disc 34 so that the drive arms can shift radially inwardly and outwardly at certain times. At their inner ends, the drive arms 46 carry upturned inclined extensions 48 adapted for camming engagement with the bullet-like cam post 23. At their outer ends, the drive arms carry ball heads 49. The extensions 48 extend into the slots 37 of stationary tube 36 so as to restrain the disc 34 from rotating with the sleeve 26 and cup 20 during the operation of the pump. The arms 46 are of a proper thickness to engage closely in the spiral slit 27 without binding therein during rotation of the sleeve 26. The ball head 49 at the outer ends of the drive arms 46 being enlarged cannot pass through the slit 27 from the outside to the inside of the rotating sleeve 26, except near the upper and lower ends of the sleeve where the widened slit sections 30 and 29 are provided.

With the pancake motor 17 in operation and the square output shaft 18 rotating the drive cup 20 in the proper direction, the sleeve 26 is rotationally driven in the same direction inside of the relatively stationary outer shell 15 to which the stationary slotted guide tube 36 is attached through the cover plate 39. Assuming the ball heads 49 to be outwardly of the rotating sleeve 26 as in FIG. 2, the rotation of the sleeve will feed the disc 34 upwardly within the shell 15 toward the top cover plate 39.

Figure 4B:
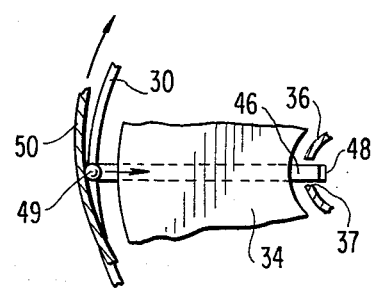
FIG. 4B is a further cross sectional view, similar to FIG. 4A, showing a further stage of movement of the radially shiftable driving element by camming means.
Figure 6:
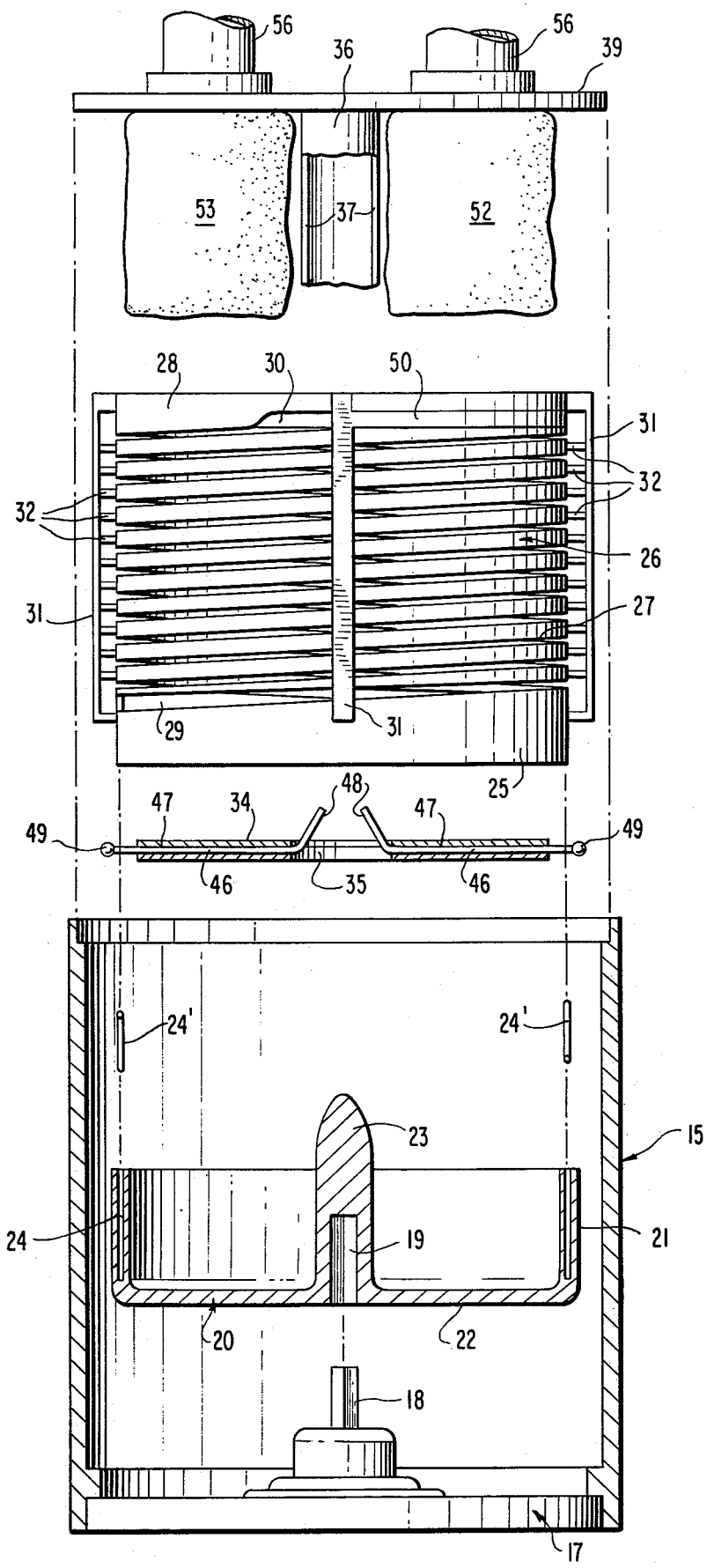
FIG. 6 is an exploded cross sectional view of the device with parts in elevation and parts broken away.

Near the top of the rotating sleeve 26, eccentric curved coil sections 50 on diametrically opposite sides of the sleeve 26 and adjacent the widened slit sections 30 engage the ball heads 49 of the two drive arms 46 and gradually force the drive arms radially inwardly through the slot sections 30 until the ball heads 49 are inside of the rotating sleeve 26 as shown in phantom lines in FIG. 2. The outermost ends of the elements 50 are anchored to the outer faces of one pair of bars 31, FIG. 4, and it may be seen that the elements 50 form rotational eccentric cams which gradually move the ball heads 49 to the interior of the sleeve 26. The movement of the ball heads inwardly by camming action of the elements 50 begins in FIG. 4A, continues in FIG. 4B, and is completed in FIG. 4, where the ball heads 49 ride over the innermost portions 51 of the camming elements 50, FIG. 4, where these elements lap the cylindrical coils or sections of the sleeve 26. At no time during the operation do the drive arms 46 completely separate from the slotted stationary guidance sleeve 36 which prevents rotation of the disc 34 with the drive arms. The continued engagement of the drive arms 46 with the guidance slots 37 can be seen in FIGS. 4, 4A and 4B.

When the ball heads 49 are inside of the sleeve 26, the disc 34 begins to descend through the sleeve 26, and the rate of descent will depend upon the volume (i.e. pressure) of venous blood pooled in the left and right atria 44 and 45. Therefore, the rate of descent of the disc 34 is a function of preload in the invention, as previously noted, with sac compliance, weight of sac and plate 34 components, and ratio of sac vetical-transverse dimensions comprising modifiable factors affecting rate of descent.

Rotation of the slitted drive sleeve 26 continues in the same direction as the disc 34 descends through it. When the drive arm extensions 48 reach the level of the bullet-like cam post 23, they will engage this post and be shifted radially outwardly by a smooth camming action until the ball heads 49 pass through the widened slit portions 29, FIG. 2, and are again disposed outwardly of the rotating sleeve 26. This condition is shown in broken lines in FIG. 2. During upward movement of the disc 34, the ball heads 49 cannot again pass to the interior of the sleeve 26 because the slit 27 is too narrow to permit this. During rotation of the sleeve 26, the attached bars 31 move with it and the spaces 33 on these bars are large enough to clear the ball heads 49, FIG. 2. It might also be noted that the upright cam post 23 projects through the lower open end of the stationary sleeve 36.

Left and right ventricle simulating sacs 52 and 53 are provided in the pumping device and are formed of pliable blood compatible material, such as Dacron reinforced Silastic. The bottom walls 54 of these sacs are suitably attached to the top of the disc 46. Each ventricular sac has a top outlet for blood and an inlet opening for blood return and these inlet and outlet openings designated 55, FIG. 2, register with the previously-described openings 41 of the lid or cover plate 39. Each sac opening 55 is coupled with a sleeve housing 56 for a conventional one-way closing and one-way opening caged ball check valve 57, the four valves 57 operating in the device exactly as described in the referenced U.S. Pat. No. 4,004,299. One check valve 57 of each sac 52 and 53 is outwardly opening and thus simulates the semilunar valve of the natural heart. The other check valve 57 of each ventricular sac is inwardly opening and outwardly closing. Thus, the valve 57 for the left ventricle sac 52 simulates the mitral valve of the heart, while the corresponding valve for the right ventricle sac 53 simulates the tricuspid valve of the heart.

The previously-noted left atrium and right atrium elements 44 and 45 are also formed of Dacron reinforced Silastic or the like, and these two elements are adapted for connection by known surgical methods to the pulmonary veins or left atrial remnant and the superior and inferior vena cava or right atrial remnant, respectively, not shown in the drawings.

The basic mode of operation of the pumping device has already been described in connection with the cam activated radial movement of the drive arms 46 by the elements 23 and 50 near the top and bottom of the rotary slitted sleeve 26. It can be readily understood that while the motor 17 is continuously driving the cup 20 and slitted sleeve 26 in one direction of rotation, the disc 34 will translate axially of the housing 15 upwardly and downwardly to cyclically compress the two sacs 52 and 53 to expel blood, followed by relaxation of the two sacs during the descent of the disc 34 so that the sacs will be filled with blood. As noted, the rate of descent of the disc 34 is dependent upon the filling pressure of the venous blood pooled in the left and right atria 44 and 45 and thus a function of preload. The purpose of the spring means 24' between the driving cup 20 and sleeve 26 is partly to cause the pump to diminish stroke volume when confronted with a large afterload, that is, high pressure in the aorta 42 or pulmonary artery 43 but also to return sleeve 26 to its resting, post-ejection, early diastolic position. This is accomplished in the following manner. The degree to which the spring means 24' or equivalent elastic means yields is a function of both time and resistance to the ascent of the disc 34. With greater load, rotation of the drive shaft 18 slows, prolonging the duration of systole (emptying). An equivalent elastic means which could be employed in lieu of the spring means 24' involves extending the bars 31 downwardly below the sleeve 26 to enter hydraulic wells in the side wall of cup 20. Also, the greater the afterload, the more rapidly the skirt 25 will descend into the slotted cup side wall 21. As a result, when confronted with a great afterload, the device will automatically reduce the stroke volume, and therefore will avoid stalling, and also will automatically correct the high pulmonic and/or systemic pressure, since this pressure is a function of stroke volume, strokes per minute (rate), and resistance. Other factors affecting duration of systole, and consequently stroke volume, include unloaded motor R.P.M., motor power, and slit 27 groove pitch.

In summary, the device automatically adjusts its pumping rate subject to both preload and afterload and in addition modifies its stroke volume in a downward direction when confronted with a high afterload. In each instance, these automatic mechanisms are a matter of degree, depending upon the above variables, and operate without electronic controls or other external controls.

It should be noted that the device can be used in a modified form as a left atrium to aorta assist device or as a right atrium to pulmonary artery assist device.

The invention may also have utility apart from the cardiovascular system per se. For example, it may be used as a single chambered pump, with a single sac, in conjunction with a membrane oxygenator, one pump forcing blood into the oxygenator and a second pump forcing blood back into the patient. A single chambered version of the device could also be used in perfusing the coronary arteries.

The invention may also have some industrial application as where automatic response to preload and afterload are desired along with pulsatile flow.

Finally, it should be noted that the invention finds utility in counterpulsation. More particularly, the device is suitable for inflating and deflating an intra-aortic balloon for counterpulsation, and offers at least two advantages over existing means. The first advantage is greater diastolic assist quantitatively when diastolic pressure is low, this feature being a function of the fact that stroke volume is related to afterload. The second advantage is avoidance of excessive diastolic pressure during counterpulsation, a feature which is automatic with the device, since its stroke volume can be set to automatically diminish in a linear manner as a function of high afterload. In other words, the device when utilized in counterpulsation affords automatic features regulating the degree of diastolic assist proportional to need. Rupture of the aorta through pressure overload would, therefore, be less of a problem with this device than with devices currently used, and the degree of diastolic augmentation would automatically be increased whenever diastolic pressure falls to low levels. This feature is not present in any known device.

It is to be understood that the form of the invention herewith shown and described is to be taken as a preferred example of the same, and that various changes in the shape, size and arrangement of parts may be resorted to, without departing from the spirit of the invention or scope of the subjoined claims.

I claim:

1. A cardiac pumping unit or the like comprising a housing, a driving motor coupled to the housing and having an output rotary shaft within the housing, a slitted sleeve coupled to the output shaft and rotating therewith and having a continuous spiral slit with widened slit sections near opposite ends of the sleeve, a translatable drive disc for movement axially of the sleeve and housing, radially shiftable drive arms on the drive disc and engageable drivingly with the spiral slit of the rotary sleeve, the drive arms having outer end head elements of a form resisting passage through said slit but being able to pass through said widened slit sections, camming means for said drive arms on the sleeve near the widened slit sections at one end of the sleeve and operable to force said head elements to the interior of the sleeve, a camming means near the other end of the sleeve engageable with the drive arms during movement of the drive disc away from the last-named end of the sleeve and shifting the head elements through the widened slit sections at said other end to the exterior of the sleeve, means continually coupled with said disc and resisting rotation of the disc with said sleeve, pliable fluid chamber means disposed within the housing between the disc and one end of the housing, and one-way opening and one-way closing check valve means connected with said pliable fluid chamber means to control the outflow and inflow of fluid from and to the pumping unit.

2. A cardiac pumping unit as defined in claim 1, and said pliable fluid chamber means comprising a pair of sacs each having an end wall secured to said drive disc and each having a fluid outflow and a fluid inflow opening, said check valve means including one outwardly opening and inwardly closing and one inwardly opening and outwardly closing check valve coupled with said sac fluid outflow and fluid inflow openings.

3. A cardiac pumping unit as defined in claim 1, wherein said drive disc is inside of the slitted sleeve and said pliable fluid chamber means is also inside of said sleeve and connected with the drive disc.

4. A cardiac pumping unit as defined in claim 1, and the first-named camming means on said sleeve comprising a pair of diametrically opposed curved eccentric wall portions on the sleeve for gradually camming said head elements through said widened slit sections from the outside to the inside of the sleeve.

5. A cardiac pumping unit as defined in claim 1, wherein the second-named camming means comprises an axially extending tapered cam element in the paths of movement of the interior ends of the drive arms and engaging the drive arms to shift them radially outwardly.

6. A cardiac pumping unit as defined in claim 1, and said second-named camming means comprising a central axial tapered post within the housing, and a pair of coacting interior inclined ends on the drive arms engageable with the tapered post during movement of the disc for shifting the drive arms radially outwardly.

7. A cardiac pumping unit as defined in claim 1, and a drive cup intervened between the output rotary shaft and said slitted sleeve and having a side wall slot receiving one end portion of the sleeve drivingly.

8. A cardiac pumping unit as defined in claim 7, and resilient means on the drive cup engaging the adjacent end of the slitted sleeve and urging it in one direction axially away from said drive cup.

9. A cardiac pumping unit as defined in claim 1, and a drive cup directly driven by said output rotary shaft and drivingly coupled with one end of the slitted sleeve and having yielding means urging the slitted sleeve in one direction axially of said housing.

10. A cardiac pumping unit as defined in claim 1, and said means continually coupled with said disc and resisting rotation of the disc comprising a longitudinally slotted sleeve coupled fixedly to the housing and disposed at the center of the housing axially thereof, and said drive arms having inner ends guidingly engaged with slots of said slotted sleeve.

11. A cardiac pumping unit as defined in claim 1, and a plurality of longitudinal stabilizing bars attached fixedly to the exterior of the slitted sleeve at circumferentially spaced points thereon, said stabilizing bars having lateral passageways for said head elements during rotation of the slitted sleeve.

12. A cardiac pumping unit as defined in claim 6, and a drive cup intervened between one end of the slitted sleeve and said output rotary shaft and drivingly coupled to said shaft, said central axial tapered post being secured to said cup centrally thereof, and the cup having a side wall annular slot receiving an end skirt of the slitted sleeve drivingly.

* * * * *